United States Patent [19]

Matsuura et al.

[11] 4,176,125

[45] Nov. 27, 1979

[54] PROCESS FOR PRODUCING 1,4-DIHYDROANTHRAQUINONE

[75] Inventors: Ryo Matsuura, Yamato; Shuichi Nakatani; Yukio Nomiyama, both of Yokohama; Tadashi Ninomiya, Kawasaki, all of Japan

[73] Assignee: Kawasaki Kasei Chemicals Ltd., Tokyo, Japan

[21] Appl. No.: 852,432

[22] Filed: Nov. 17, 1977

[51] Int. Cl.$^2$ .............................................. C07C 49/68
[52] U.S. Cl. .................................... 260/369; 260/367
[58] Field of Search ............................. 260/396 R, 369

[56] References Cited

U.S. PATENT DOCUMENTS

| | | | |
|---|---|---|---|
| 1,890,040 | 12/1932 | Luttringhaus et al. | 260/396 R |
| 2,938,913 | 5/1960 | Weyker et al. | 260/369 |
| 3,778,452 | 12/1973 | Jasey et al. | 260/369 |
| 3,838,178 | 9/1974 | Vaughn | 260/369 |

FOREIGN PATENT DOCUMENTS 1224885  6/1960  France ........................ 260/369

*Primary Examiner*—Vivian Garner
*Attorney, Agent, or Firm*—Oblon, Fisher, Spivak, McClelland & Maier

[57] ABSTRACT

1,4-Dihydroanthraquinones are produced by oxidizing 1,4,4a,9a-tetrahydroanthraquinone or 1,4-dihydroanthrahydroquinone or an inert substituted derivative thereof with molecular oxygen in an aqueous medium at the reaction temperature of lower than 70° C. under the condition of pH of 8.5 to 12.

3 Claims, No Drawings

PROCESS FOR PRODUCING 1,4-DIHYDROANTHRAQUINONE

BACKGROUND OF THE INVENTION

1. Field of the Invention

The present invention relates to a process for producing 1,4-dihydroanthraquinones. More particularly, it relates to a process for producing 1,4-dihydroanthraquinones by oxidizing 1,4,4a,9a-tetrahydroanthraquinone or 1,4-dihydroanthrahydroquinone or an inert substituted derivative.

2. Description of the Prior Art 1,4-Dihydroanthraquinones are important starting materials for producing agrochemicals, dyes and other fine chemicals and also useful as agrochemicals by themselves.

Heretofore, it has been known to produce 1,4-dihydroanthraquinone (1,4-DHAQ) by several processes as follows.

(1) 1,4,4a,9a-Tetrahydroanthraquinone (THAQ) is oxidized in ethanol with ferric chloride;

(2) THAQ is oxidized with ferric chloride in the presence of a wetting agent (Chemical Abstract 56, 7237$^e$ (1962));

(3) THAQ is oxidized with potassium bromate (Chemical Abstract 52, 12830$^b$ (1958));

(4) THAQ is oxidized with a gaseous oxygen in an aqueous medium at pH of 4 to 8 preferably 6 to 7 at 85° to 100° C. preferably 90° to 95° C. (B. Pat. No. 896,911 (Mar. 23, 1962)).

In the processes (1) and (2), expensive ferric chloride is used to cause the high cost. The process (3) is an experimental process and is not an industrial process. The process (4) is superior to the other processes as an industrial process. However, the reaction velocity is remarkably low to need longer than 4 hours and the purity of the resulting 1,4-DHAQ is 96% as maximum.

The inventors have studied various process for producing 1,4-DHAQ having high purity from THAQ with industrial advantages. As the result, the inventors have found that when the pH is higher than that of the process (4) and the temperature is lowered in the case of the oxidation of THAQ with molecular oxygen in an aqueous medium, the reaction is accelerated and the reaction time is remarkably shortened and the amount of the by-product of anthraquinone can be reduced, surprisingly.

SUMMARY OF THE INVENTION

It is an object of the present invention to provide a process for producing 1,4-dihydroanthraquinones at high reaction velocity.

It is another object of the present invention to provide a process for producing 1,4-dihydroanthraquinones having high purity without using an expensive oxidizing agent.

The foregoing and other objects of the present invention have been attained by producing 1,4-dihydroanthraquinones by oxidizing 1,4,4a,9a-tetrahydroanthraquinone or 1,4-dihydroanthrahydroquinone or an inert substituted derivative thereof with molecular oxygen in an aqueous medium at the reaction temperature of lower than 70° C. under the condition of pH of 8.5 to 12, optionally, in the presence of a quinone type redox catalyst.

DETAILED DESCRIPTION OF THE PREFERRED EMBODIMENTS 1,4-Dihydroanthraquinones include inert substituted derivatives thereof which have a substituent such as alkyl group such as $C_1$–$C_8$ alkyl group; or halogen atom such as chlorine; bromine atom; haloalkyl group or phenyl group (hereinafter referring to as 1,4-DHAQs) (non-substituted 1,4-dihydroanthraquinone is referred to as 1,4-DHAQ).

1,4,4a,9a-Tetrahydroathraquinones include inert substituted derivatives which have the same substituent (hereinafter referring to as THAQs) (non-substituted 1,4,4a,9a-tetrahydroanthraquinone is referred to as THAQ).

1,4-Dihydroanthrahydroquinones include inert substituted derivatives which have the same substituent (hereinafter referring to as 1,4-DHAHQs) (non-substituted 1,4-dihydroanthrahydroquinone is referred to as 1,4-DHAHQ).

In order to simplify the description, it will be mainly discussed on 1,4-DHAQ, THAQ and 1,4-DHAHQ since the inert substituted derivatives have similar characteristics in the reaction.

The first feature of the invention is to produce 1,4-DHAQs by oxidizing THAQs or 1,4-DHAHQs with molecular oxygen in an aqueous medium at the reaction temperature of lower than 70° C. under the condition of pH of 8.5 to 12.

The second feature of the invention is to produce 1,4-DHAQs by oxidizing THAQs or 1,4-DHAHQs with molecular oxygen in an aqueous medium at the reaction temperature of lower than 70° C. under the condition of pH of 8.5 to 12 in the presence of a quinone type redox catalyst.

The first feature of the invention will be illustrated in detail.

THAQs used in the process of the present invention can be easily obtained as addition compounds of naphthoquinone and a diene produced by the Diels-Alder reaction.

The dienes can be ones disclosed in British Pat. No. 896,911. Suitable dienes include butadiene, alkyl substituted butadienes such as isoprene, 2,3-dimethyl butadiene, 2-butyl butadiene; halogen substituted butadienes such as 2-chlorobutadiene, 2-bromobutadiene; phenyl substituted butadienes such as 2-phenylbutadiene; cyclopentadienes and pentadienes. 1,4-Dihydroanthrahydroquinones can be easily obtained by treating the addition compounds obtained by the Diels-Alder reaction with a catalytic amount of a base such as alkali metal hydroxide and ammonia or an acid such as chloroacetic acid in an aqueous medium or an organic medium.

As the starting material, THAQs or 1,4-DHAHQs can be used.

The reaction velocity is relatively faster when 1,4-DHAHQs are used. However, THAQs are usually used because of an elimination of the isomerization step. It is preferable to use finely divided powder obtained by pulverizing it.

As the aqueous medium, water is usually used. It is possible to dissolve a small amount of a salt in water or to add an inert organic solvent such as alcohols to water. With the reaction is accelerated with the additive, the addition of the additive is advantageous.

The molecular oxygen is usually air from the economical viewpoint.

The typical process of the present invention is as follows.

For example, an aqueous medium is charged in a vessel equipped with a stirrer and a gas inlet and pH is adjusted to 8.5 to 12 with a pH modifier, and then, the starting material of THAQs or 1,4-DHAHQs is dispersed. The concentration of the starting material is adjusted to about 1 to 20 wt.%. It is also possible to disperse the starting material in an aqueous medium and then to adjust pH to 8.5 to 12 with a pH modifier.

Of course, when the starting material is obtained as an aqueous slurry in the previous step, it can be used without separating it.

In the above condition, the starting material of THAQs or 1,4-DHAHQs is not completely dissolved to form a slurry. Air is fed from the gas inlet into the aqueous slurry at the reaction temperature of 10° to 70° C. preferably 30° to 60° C. During the reaction, the mixture is stirred so as to thoroughly contact the gas-liquid-solid components. The reaction mixture is white or purplish white at the initiation and is changed to dark purple caused by quinhydrone and is further changed to yellowish color caused by continuing the oxidation. When it is substantially converted to 1,4-DHAQs, the reaction is completed to form the specific yellowish crystals. Air is further fed for several minutes and the reaction is finished in less than 3 hours, usually 10 to 120 minutes. During the reaction, most of the starting material and the product are present in the form of suspension. Accordingly, it is effective to stir with high shear and/or to add a surfactant for smoothly performing the reaction.

The reaction product is filtered and washed with water and dried in nitrogen flow.

The melting point and the infrared spectrum of the resulting 1,4-DHAQs are the same as those of 1,4-DHAQs produced by the conventional process using ferric chloride. The infrared spectrum of the starting material of THAQs or 1,4-DHAHQs is remarkably different from that of the product of 1,4-DHAQs. Accordingly, they can be easily identified. The filtrate can be reused after adjusting pH.

The process of the present invention can be also applied for 1,4,4a,9a-tetrahydroanthraquinone having a substituent or 1,4-dihydroanthrahydroquinone having a substituent.

The pH modifiers can be ones for adjusting the pH to 8.5 to 12 which are inert to the starting material and the product.

Suitable pH modifiers include alkali metal hydroxides such as sodium hydroxide, potassium hydroxide; alkali metal carbonates such as sodium carbonate, potassium carbonate; ammonia and alkyl amines such as diethylamine, triethyl amine, etc.

In order to maintain the pH during the reaction, it is possible to add buffer agents such as a mixture of boric acid and potassium chloride or a phosphate.

It is preferable to maintain the pH in a range of 8.5 to 12. When the pH is lower than from 8.5 to 7, the reaction velocity becomes slow. When the pH is higher than 12, the product of 1,4-DHAQs is further oxidized to produce anthraquinones (hereinafter referring to as AQ), and the resulting product of 1,4-DHAQs is contaminated with AQ. When the pH is higher than 13, the product of 1,4-DHAQs is substantially converted to AQ.

The reaction temperature is lower than 70° C. preferably in a range of 30° to 60° C. At a temperature of lower than 10° C., it is possible to decrease the amount of AQ to less than 0.1 wt.%, however, the reaction velocity is too slow. At a temperature of higher than 70° C., AQ is easily produced to decrease the purity of the product. At a temperature of 30° to 60° C., the reaction velocity is fast and the velocity for producing AQ is slow advantageously.

The second feature of the invention will be illustrated in detail.

The quinone type redox catalysts used in the process of the invention can be water soluble quinones such as 1,4-napthoquinone-2-sulfonates, 1,2-naphthoquinone-4-sulfonates, anthraquinone disulphonates etc.

The cation components forming the salts can be alkali metals such as sodium, potassium and ammonium. In the use of the quinone redox catalysts, they can be either the quinone type for oxidation form or the hydroquinone type for reduction form.

An amount of the quinone type redox catalyst is less than 1 mole usually in a range of 0.01 to 0.1 mole per 1 mole of the starting material in the solution. When the amount of the redox catalyst is smaller, the effect is not enough. On the other hand, when the amount of the redox catalyst is larger, it is not economical. When the quinone type redox catalyst is used, the reaction time can be shortened to $\frac{1}{2}$ to $\frac{1}{3}$ under the same conditions of pH, reaction temperature and concentration in comparison with that of the first feature of the invention. Moreover, the formation of AQ can be inhibited by the addition of the quinone type redox catalyst.

It is also preferable to maintain a pH of 8.5 to 12. The reaction temperature is lower than 70° C. preferably higher than 5° C. especially in a range of 30° to 60° C.

As the first feature of the invention, when the reaction is performed at low temperature, it is effective for lowering the formation of AQ to less than 0.5 wt.%. However, the low reaction temperature is not advantageous from the viewpoint of the thermal economy and the equipments to cause higher cost of the product. The reaction temperature is optimum in a range of 30° to 60° C.

The quinone type redox catalyst is usually added to the slurry before the reaction, that is, before feeding molecular oxygen. Thus, when the filtrate obtained by separating 1,4-DHAQ after the reaction is used, it is enough to replenish a part of the catalyst.

In the second feature of the invention, the starting materials of THAQs and 1,4-DHAHQs and the aqueous medium, the molecular oxygen and the pH modifiers can be the same ones.

In accordance with the first feature of the invention, the reaction velocity can be improved and the purity of the product of 1,4-DHAQs can be increased in comparison with those of the conventional process.

In accordance with the second feature of the invention, the reaction velocity can be increased to shorten the reaction time to $\frac{1}{2}$ to $\frac{1}{3}$ and the purity of 1,4-DHAQ can be further increased in comparison with those of the process of the first feature.

The present invention will be illustrated by certain examples and references in detail.

EXAMPLE 1

In a reactor equipped with a stirrer, 2.12 wt. parts of sodium carbonate was dissolved in 100 wt. parts of water, and 2.12 wt. parts of THAQ was added while stirring the solution. The mixture was in a form of slurry having a pH of 11.3.

The mixture was heated to 50° C. and air was fed into the mixture while thoroughly stirring to react them. During the reaction, the white slurry was changed to purplish color and changed to dark purple color of quinhydrone (adduct of 1,4-DHAHQ and 1,4-DHAQ) and then changed to yellowish color and finally changed to the specific yellow slurry of 1,4-DHAQ. The color of the slurry was not further changed. At the above condition, the feed of air was stopped to complete the reaction. The reaction time was 1 hour and pH at the end of the reaction was 10.3.

The reaction product was filtered and washed with water and dried in nitrogen flow to obtain 2.06 wt. parts of yellow crystals of crude 1,4-DHAQ. The yield was 98 mole %.

The product had a melting point of 204° to 208° C. It was found by the high speed liquid chromatography that the product contained 2.1 wt.% of AQ.

The product was recrystallized from ortho-xylene to obtain purified 1,4-DHAQ having a melting point of 208.5° to 209.5° C. which was the same with the data of prior art reference. It was further confirmed by the infrared spectrum analysis that the product was 1,4-DHAQ.

In the mixed examination of the product and 1,4-DHAQ obtained by the known process oxidizing with ferric chloride, any difference of the melting point was not found.

EXAMPLE 2

In accordance with the process of Example 1 except using 1,4-DHAHQ instead of THAQ, the reaction was carried out to obtain 2.05 wt. parts of crude 1,4-DHAQ. It was confirmed by the infrared spectrum analysis, that the product was 1,4-DHAQ. It was found by the high speed liquid chromatography that the product contained 2.0 wt.% of AQ.

EXAMPLE 3

In accordance with the process of Example 1 except using 2.40 wt. parts of 2,3-dimethyl-1,4,4a,9a-tetrahydroanthraquinone instead of THAQ, the reaction was carried out to obtain 2.33 wt. parts of the product having a melting point of 199° to 202° C. It was confirmed by the infrared spectrum analysis that the product was 2,3-dimethyl-1,4-dihydroanthraquinone. The content of 2,3-dimethylanthraquinone was 2.2 wt.%.

EXAMPLE 4

In the reactor, 0.2 mole of boric acid, 0.2 mole of potassium chloride, sodium hydroxide and water were mixed to prepare a buffer solution having a pH of 9.

A 2.12 wt. parts of THAQ was added to 100 wt. parts of the buffer solution and air was fed into the mixture at 50° C. for 2 hours under stirring to react them. The reaction mixture was treated in accordance with the process of Example 1 to obtain 2.05 wt. parts of the product having a melting point of 204° to 208° C. which was the same as that of Example 1. It was confirmed by the infrared spectrum analysis that the product was 1,4-DHAQ. The content of AQ in the product was 2.2 wt.%.

Reference 1

A 2.12 wt. parts of THAQ was added to 100 wt. parts of a buffer solution having a pH of 7 (0.2 mole of potassium dihydrogen phosphate, sodium hydroxide and water) and air was fed into the mixture at 50° C. for 2 hours under stirring to react them. The reaction mixture was treated in accordance with the process of Example 1. It was found by the infrared spectrum analysis that the product was substantially the unreacted material.

The product was further oxidized with air under the same condition for 4 hours. However, the mixture did not change to the specific yellow slurry of 1,4-DHAQ which indicates the completion of the reaction. It was found by the infrared spectrum analysis that the product was substantially the unreacted material.

Reference 2

A 2.12 wt. parts of THAQ was added to 100 wt. parts of an aqueous solution of sodium hydroxide having a pH of 13, and air was fed into the mixture at 50° C. for 1 hour under stirring to react them. The reaction mixture was treated in accordance with the process of Example 1 to obtain 2.05 wt. parts of yellowish orange crystals. It was found by the high speed liquid chromatography analysis that the content of AQ in the product was 62 wt.%.

EXAMPLE 5

In accordance with the process of Example 1 except feeding air at 30° C. for 2 hours, the reaction was carried out to obtain 2.06 wt. parts of the product having a melting point of 204° to 208° C. which was the same as that of Example 1. The content of AQ in the product was 2.0 wt.%.

EXAMPLE 6

In a reactor equipped with a stirrer, 4.24 wt. parts of sodium carbonate was dissolved in 100 wt. parts of water and then, 8.48 wt. parts of THAQ was added to the mixture under stirring and the pH was adjusted to 11.6 by adding 1N-NaOH aq. sol.

The mixture was heated to 50° C. and air was fed into the mixture with stirring to react them. After about 60 minutes, the dark purple slurry was changed to the specific yellow slurry of 1,4-DHAQ. Air was further fed and the reaction was stopped after 80 minutes from the initiation.

The reaction mixture was treated in accordance with the process of Example 1 to obtain 8.19 wt. parts of yellow crystals as the product.

The product had a melting point of 204° to 208° C. It was found by the high speed liquid chromatography that the content of AQ was 2.2 wt. %. It was confirmed by the infrared spectrum analysis that the product was 1,4-DHAQ.

Reference 3

In accordance with the process of Example 1 except feeding air at 80° C. for 1 hour, the reaction was carried out to obtain yellowish orange crystals. It was found by the high speed liquid chromatography analysis that the content of AQ in the product was 40 wt.%.

EXAMPLE 7

In a reactor equipped with a stirrer, 4.24 wt. parts of sodium carbonate was dissolved in 100 wt. parts of water and then, 8.48 wt. parts of THAQ was added to the mixture under stirring and then, 0.26 wt. part of sodium 1,4-naphthoquinone-2-sulfonate (referring to as NQSNa) was added and the pH was adjusted to 11.3 by adding 1N-NaOH aq. sol.

The mixture was heated to 50° C. and air was fed into the mixture under stirring to react them. After about 30 minutes, the dark purple slurry was changed to the specific yellow slurry of 1,4-DHAQ. The color was not further changed. The reaction was stopped after 45 minutes from the initiation. The reaction mixture was treated in accordance with the process of Example 1 to obtain 8.24 wt. parts of yellow crystals having a melting point of 206° to 208.5° C. It was found by the high speed liquid chromatography analysis that the content of AQ was 1.1 wt.% It was confirmed by the infrared spectrum analysis that the product was 1,4-DHAQ.

EXAMPLE 8

In accordance with the process of Example 7 except feeding air at 20° C., the reaction was carried out. After 1 hour, the slurry was changed from the dark purple slurry to yellowish slurry. After 2 hours, it was completely changed to the specific yellow slurry of 1,4-DHAQ and the feed of air was stopped.

The reaction mixture was treated in accordance with the process of Example 1 to obtain 8.22 wt. parts of yellow crystals having a melting point of 206° to 208.5° C. It was found by the high speed liquid chromatography analysis that the content of AQ was 1.0 wt.%.

The process was repeated except using 1,4-DHAHQ as the starting material instead of THAQ. The results were the same. In the experiments, the infrared spectra of the compounds were identified with those of the prior art.

What is claimed is:

1. In a process for producing 1,4-dihydroanthraquinones by oxidizing 1,4,4a,9a-tetrahydroanthraquinone or 1,4-dihydroanthrahydroquinone which may contain inert substituents with molecular oxygen, the improvement which comprises carrying out said oxidation at a reaction temperature of from 10° C. to 70° C. and a pH of 8.5 to 12 in an aqueous medium in the presence of a quinone type redox catalyst, said inert substituents being selected from the group consisting of $C_1-C_8$ alkyl, halogen, haloalkyl, and phenyl.

2. The process of claim 1, wherein said quinone type redox catalyst is selected from the group consisting of 1,4-naphthoquinone-2-sulfonates, 1,2-naphthoquinone-4-sulfonates and anthraquinone disulfonates.

3. The process of claim 2 wherein 1,4,4a,9a-tetrahydroanthraquinone is oxidized and the quinone type redox catalyst is sodium 1,4-napthoquinone-2-sulfonate.

* * * * *